United States Patent
Kinoshita et al.

(10) Patent No.: US 8,591,561 B2
(45) Date of Patent: Nov. 26, 2013

(54) HAIR-GROWTH ADJUSTING LIGHT EMITTING DEVICE

(75) Inventors: Masato Kinoshita, Osaka (JP); Chosei Hamada, Osaka (JP); Yasuhiro Satou, Hyogo (JP); Kaname Okuno, Hyogo (JP); Masako Yamasaki, Hyogo (JP); Kaori Suzuki, Osaka (JP)

(73) Assignee: Panasonic Corporation (JP)

( * ) Notice: Subject to any disclaimer, the term of this patent is extended or adjusted under 35 U.S.C. 154(b) by 149 days.

(21) Appl. No.: 12/935,091

(22) PCT Filed: Mar. 26, 2009

(86) PCT No.: PCT/IB2009/005070
§ 371 (c)(1),
(2), (4) Date: Mar. 30, 2011

(87) PCT Pub. No.: WO2009/118617
PCT Pub. Date: Oct. 1, 2009

(65) Prior Publication Data
US 2012/0065708 A1    Mar. 15, 2012

(30) Foreign Application Priority Data
Mar. 28, 2008    (JP) ................................. 2008-087881

(51) Int. Cl.
*A61N 5/06* (2006.01)
*H05B 41/30* (2006.01)

(52) U.S. Cl.
USPC ................................................ 607/88; 606/9

(58) Field of Classification Search
USPC ................... 606/2, 9, 13; 607/88–95; 429/97; 200/50.05, 51.08
See application file for complete search history.

(56) References Cited

U.S. PATENT DOCUMENTS

| | | | |
|---|---|---|---|
| 3,644,818 A | 2/1972 | Paget | |
| 4,506,454 A | 3/1985 | Kerschgens | |
| 5,149,604 A * | 9/1992 | Nakanishi | 429/97 |
| 5,680,926 A * | 10/1997 | Sandor et al. | 200/51.08 |

(Continued)

FOREIGN PATENT DOCUMENTS

| | | |
|---|---|---|
| EP | 1 433 499 A1 | 6/2004 |
| JP | H9-10336 A | 1/1997 |

(Continued)

OTHER PUBLICATIONS

Russian Notice of Allowance and English translation thereof issued in a counterpart Russian Application No. 2010139782, dated Nov. 18, 2011.

*Primary Examiner* — Sam Yao
*Assistant Examiner* — Nathan J Jenness
(74) *Attorney, Agent, or Firm* — Bacon & Thomas, PLLC

(57) ABSTRACT

A hair-growth adjusting light emitting device includes a device body, a light-emitting unit attached to the device body, and a locking unit for locking the light-emitting unit to the device body. The device body has a main capacitor, a device body connector, an electric power switch, a release switch, and an electric power supplying part. The light-emitting unit has a light-emitting body and a light-emitting body side connector. Furthermore, the hair-growth adjusting light emitting device includes a release restriction mechanism for preventing the light-emitting unit from being released by the release button when the electric power switch is at a power-on position where the electric power supplying part feeds the electric power to the main connector, and a power-on restriction mechanism for preventing the electric power switch from moving to the power-on position when the light-emitting unit is detached from the device body.

10 Claims, 15 Drawing Sheets

(56) References Cited

U.S. PATENT DOCUMENTS

| | | |
|---|---|---|
| 2002/0139654 A1 | 10/2002 | Jong |
| 2004/0097777 A1 | 5/2004 | Hughett et al. |
| 2007/0260298 A1 | 11/2007 | Naldoni |

FOREIGN PATENT DOCUMENTS

| | | |
|---|---|---|
| JP | 2000-245152 A | 9/2000 |
| JP | 2003-526485 A | 9/2003 |
| JP | 2005-509485 A | 4/2005 |
| JP | 2005278724 | 10/2005 |
| RU | 2 083 354 C1 | 7/1997 |
| WO | 82/04382 A1 | 12/1982 |
| WO | 02078786 A | 10/2002 |
| WO | 02078786 A1 | 10/2002 |
| WO | 2007007167 A | 1/2007 |
| WO | 2007007167 A1 | 1/2007 |

* cited by examiner

HAIR-GROWTH ADJUSTING LIGHT EMITTING DEVICE

FIELD OF THE INVENTION

This invention relates to a hair-growth adjusting light emitting device that irradiates a human skin with light for adjusting growth of body hair.

BACKGROUND ART

Conventionally, it is known that a hair-growth adjusting light emitting device irradiates a human skin with light emitted from a light-emitting body, such as a flash lamp, to promote growth of body hair, thereby performing depilation or hair fostering. Japanese Unexamined Patent Application Publication No. 2005-278724 discloses a hair-growth adjusting light emitting device that includes a casing gripped by a user, and a light-emitting body, such as a flash lamp, accommodated therein. The user grips the casing such that a light-emitting surface of the light-emitting body is directed to a portion of the human skin at which growth of body hair is needed to be suppressed or promoted. In this state, light is emitted from the light-emitting body, thereby performing depilation or hair fostering. In such hair-growth adjusting light emitting devices, the light-emitting body is deteriorated every time when irradiating. The deteriorated light-emitting body should preferably be replaced when the number of the irradiation times exceeds a predetermined value in order to perform effective depilation or hair fostering. From cost and environmental points of view, only the deteriorated light-emitting body is preferably replaced by a new one, not the whole hair-growth adjusting light emitting device.

By the way, the light-emitting body needs to be fastened in suitable relation to optical components such as a shade for reflecting the light from the light-emitting body and a lens for diffusing or collecting the light from the light-emitting body. Supposed that the light-emitting body and the optical components are combined to form a light-emitting unit, in the case where the deteriorated light-emitting body is replaced by a new one, the light-emitting unit may be used as the new one, thereby making it easy to replace the light-emitting body.

The light-emitting body in the light-emitting unit is configured such that a high voltage is applied thereto. Therefore, when replacing the light-emitting unit, for example, it is necessary to fully pay attention to an occurrence of sparks in an electric contact due to the high voltage. Accordingly, a replacement work of the light-emitting unit needs an operator who has received training for the replacement. As a result, there are some disadvantages that users without expert knowledge of electric appliances can hardly carry out the replacement by themselves.

SUMMARY OF THE INVENTION

The invention has been conceived in view of the above-mentioned disadvantages, and it is an object of the present invention to provide a hair-growth adjusting light emitting device in which a light-emitting unit can be replaced safely.

The hair-growth adjusting light emitting device of the present invention includes a device body, a light-emitting unit removably attached to the device body, and a locking unit for locking the light-emitting unit to the device body. The device body includes an electric power supplying part, a first connector electrically connected to the electric power supplying part, an electric power switch that switches ON and OFF of the electric power supplied from the electric power supplying part to the first connector, and a release button for releasing the lock of the light-emitting unit by the locking unit. The light-emitting unit includes a light-emitting body for irradiating a human skin with light for adjusting growth of body hair, a second connector electrically connected to the first connector when the light-emitting unit is locked to the device body and feeding electric power from the first connector to the light-emitting body. The hair-growth adjusting light emitting device further includes a release restriction mechanism for preventing the lock of the light-emitting unit from being released by the release button in the state where the electric power switch is at a power-on position where the electric power supplying part feeds the electric power to the first connector is turned on, and a power-on restriction mechanism for preventing the electric power switch from moving to the power-on position in the state where the light-emitting unit is detached from the device body.

According to the hair-growth adjusting light emitting device of the present invention, the light-emitting unit cannot be detached when the electric power switch is at the power-on position. Moreover, in the state where the light-emitting unit is removed, it is impossible to move the electric power switch to the power-on position. Accordingly, when a user, even if without expert knowledge of electric appliances, replaces the light-emitting unit, it is possible to prevent a dangerous occurrence, like sparking in an electric contact, with reliability. Consequently the replacement work is carried out safely.

Furthermore, in the hair-growth adjusting light emitting device with the above-mentioned configuration, the electric power supplying part preferably includes a booster circuit part for boosting electric power from an electric power source, a capacitor for accumulating the boosted electric power and supplying the accumulated electric power to the first connector, a discharge circuit for discharging the electric power accumulated in the capacitor, a discharge control part for controlling the discharge circuit to discharge the electric power in the capacitor when the electric power switch is switched to a power-off position where the electric power supplying part stops feeding the electric power to the first connector. Such manners may bring more safety to the hair-growth adjusting light emitting device.

BRIEF DESCRIPTION OF THE DRAWINGS

FIG. 5A is an explanatory view (top view) showing a main section of the hair-growth adjusting light emitting device when being turned on;

FIG. 5B is an explanatory view (perspective view) showing a main section of the hair-growth adjusting light emitting device when being turned on;

FIG. 5C is an explanatory view (side view) showing a main section of the hair-growth adjusting light emitting device when being turned on;

FIG. 7A is an explanatory view (top view) showing a main section of the hair-growth adjusting light emitting device in the state where the release button is pushed in;

FIG. 7B is an explanatory view (perspective view) showing a main section of the above hair-growth adjusting light emitting device in the state where the release button is pushed in;

FIG. 7C is an explanatory view (side view) showing a main section of the hair-growth adjusting light emitting device in the state where the release button is pushed in;

DESCRIPTION OF THE PREFERRED EMBODIMENT

Figure 1:
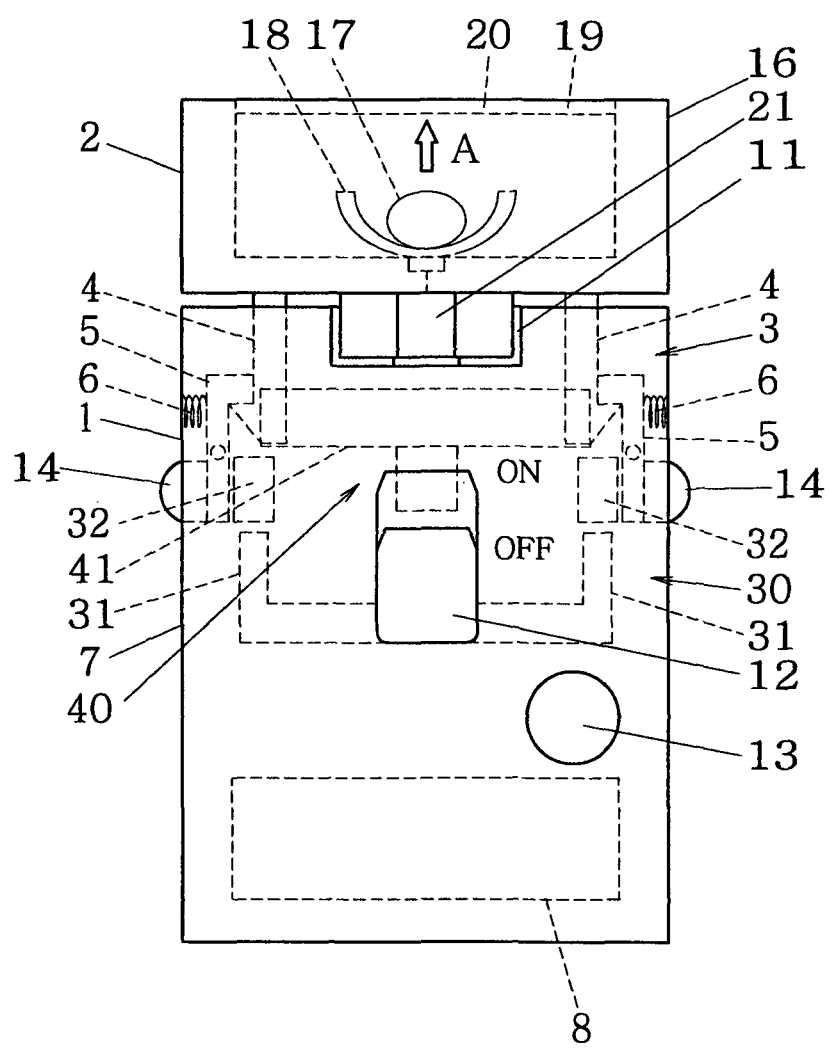
FIG. 1 is a front view of one embodiment of a hair-growth adjusting light emitting device according to the present invention.
Figure 2:
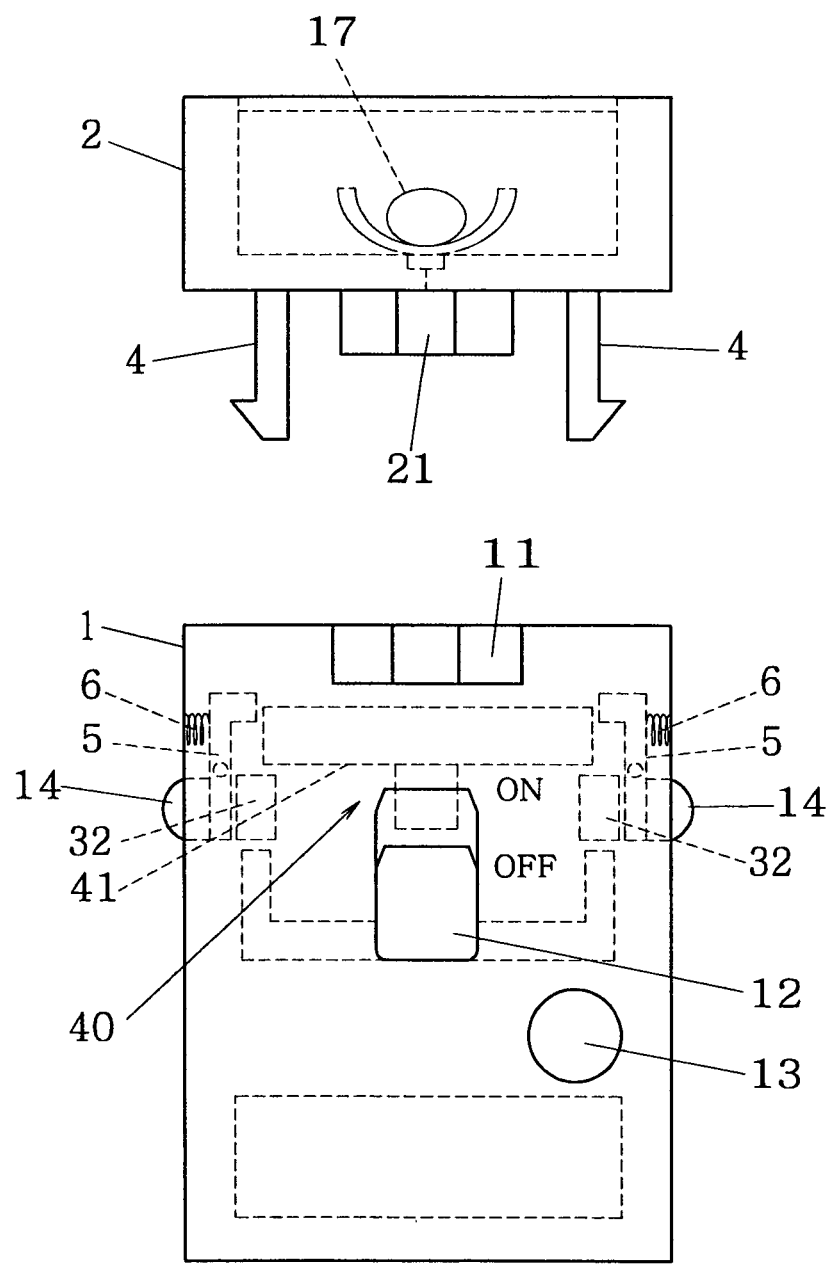
FIG. 2 is a front view of the hair-growth adjusting light emitting device with a light emitting body removed from a device body.
Figure 3:
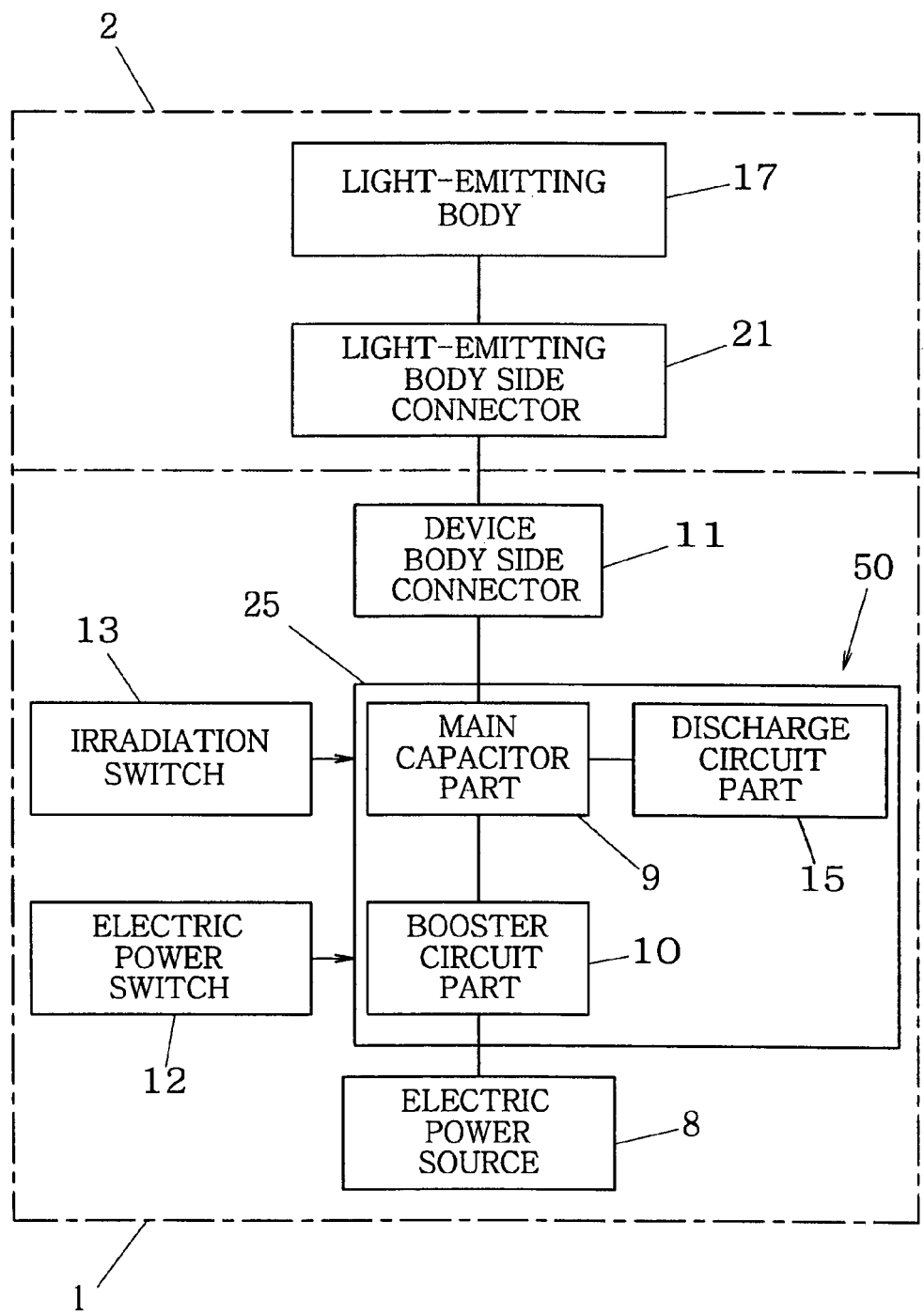
FIG. 3 is a block diagram of the hair-growth adjusting light emitting device.

Hereinafter, a hair-growth adjusting light emitting device in accordance with a preferred embodiment of the invention will be described in detail with reference to the accompanying drawings. FIGS. 1 and 2 show a whole configuration of the hair-growth adjusting light emitting device of the present embodiment. FIG. 3 shows a block diagram of the hair-growth adjusting light emitting device of the present embodiment. The hair-growth adjusting light emitting device of the present embodiment includes a device body 1 which a user can grip by one hand, a light-emitting unit 2 removably attached to the device body 1, and a locking unit 3 for locking the light-emitting unit 2 to the device body 1. In the present embodiment, the terms of "upward and downward", "left and right", and "forward and backward", which indicate directions of the hair-growth adjusting light emitting device, are defined as follows. The "upward and downward" direction of the hair-growth adjusting light emitting device corresponds to a longitudinal direction of the paper in FIGS. 1 and 2, i.e., the upward direction denotes a direction in which the light-emitting unit 2 is positioned relative to the device body 1. The "left and right" direction of the hair-growth adjusting light emitting device corresponds to a transverse direction of the paper in FIGS. 1 and 2, i.e., it denotes the direction in which two release buttons 14,14 are connected with a line. The "forward and backward" direction of the hair-growth adjusting light emitting device corresponds to a direction perpendicular to the paper plane in FIGS. 1 and 2, i.e., the front side denotes a side in which an electric power switch 12 as described later is provided, among sides of a body casing 7.

As shown in FIGS. 1 to 3, the device body 1 has a body casing 7, a device body side connector 11 as a first connector, an electric power supplying part, an electric power switch 12, and a release button 14. The electric power supplying part has an electric power source 8, a main capacitor part 9, a booster circuit part 10, a discharge circuit part 15, and a control part 25 as a discharge control part. The light-emitting unit 2 has a light-emitting body 17 and a light-emitting body side connector 21 as a second connector.

The body casing 7 has a box-shape with an inner cavity. The body casing 7 accommodates the electric power source 8, the main capacitor part 9, the booster circuit part 10, and the device body side connector 11 in the cavity. The electric power source 8 may utilize a commercial dry cell. The booster circuit part 10 boosts the voltage, which is supplied from the electric power source 8, up to a voltage needed to cause a light emission of the light-emitting body 17, then feeding the boosted voltage to the main capacitor part 9. The main capacitor part 9 accumulates the boosted electric power and feeds the accumulated electric power to the connector 11 simultaneously, when the electric power switch 12 is turned on. The connector 11 is exposed in an upper end side of the body casing 7 through an opening thereof, and connected electrically to the light-emitting body side connector 21 when the light-emitting unit 2 is locked to the device body 1. The connectors 11, 21 are made of conductive materials, for example, metal. It is noted that, for the electric power source 8, various things, such as a battery charger and a battery for exclusive use, are available besides a dry cell. Furthermore, it is preferred that the body casing 7 has, for example, an approximately tubular shape with an elliptic section so that a user can grip it easily.

The electric power switch 12, which is operated by a user, and an irradiation switch 13 are disposed in the front side of the body casing 7, being exposed. The electric power switch 12 is provided so as to slide freely in the upward and downward direction along the front side of the body casing 7. The electric power switch 12 switches between ON and OFF operations of the electric power supplying part in accordance with the slide positions. That is, the electric power supplying part feeds electric power from the booster circuit part 10 to the main capacitor part 9, when the electric power switch 12 is in an upper position (power-on position) within the front surface of the body casing 7. On the other hand, the electric power supplying part stops feeding the electric power to the main capacitor part 9, when the electric power switch 12 is in a lower position (power-off position) within the front surface of the body casing 7. An irradiation switch 13 switches between ON and OFF irradiation of light-emitting body 17, when the electric power switch 12 is in the power-on position.

As shown in FIGS. 1 and 2, a locking unit 3 includes a pair of locked parts 4, a pair of locking parts 5, and a pair of biasing members 6. The locked parts 4, 4 extend downwardly from the light-emitting unit 2, and the lower ends thereof are bent outwardly in the right and left direction, forming a pair of right and left hooks. In order to lock the locked parts 4, 4, the locking parts 5, 5 are provided in the device body 1, and the upper ends thereof are bent inwardly in the right and left direction, forming a pair of right and left hooks. The locking part 5 has a pivotal shaft at a center portion in a longitudinal direction thereof. The pivotal shaft is fixed to the device body 1 along the forward and backward direction of hair-growth adjusting light emitting device. By the pivotal shaft, the locking part 5 moves pivotally about the pivotal shaft in a seesaw fashion relative to the device body 1. The biasing member 6 is configured by a compression spring and attached to an upper end portion of the locking part 5 so as to be interposed between the locking part 5 and the body casing 7. The biasing member 6 constantly presses the upper end portion of the locking part 5 toward the inner side of the body casing 7. Thereby, in the state where the light-emitting unit 2 is attached to the device body 1, the upper end portion of the locking part 5 is constantly urged against the locked part 4 to maintain the locked condition between the locked part 4 and the locking part 5. That is, the locking unit 3 locks the light-emitting unit 2 to the device body 1 by engaging the lower end portion of the locked part 4, which is bent into an L shape, with the upper end portion of the locking part 5. The configuration for releasing the lock will be described later.

The body casing 7 includes a pair of the right and left release buttons, which are freely projected or recessed, in both of the right and left sides thereof. A portion of the release button 14 is exposed at the outside of the body casing 7, and the exposed portion is operated by a user. In the body casing 7, the release button 14 is in contact with the lower end part of the locking part 5, i.e., a portion opposite to the upper end portion with which the biasing member 6 contacts, with respect to the pivotal shaft.

As shown in FIG. 3, a control part 25 accommodated in the body casing 7 has a booster circuit part 10, a main capacitor part 9, and a discharge circuit part 15 for discharging the electric charge accumulated in the main capacitor part 9 to be zero. The control part 25 receives operation signals from the electric power switch 12 and the irradiation switch 13, and controls the light emission of the light-emitting unit 2 based on each of the received operation signals.

As shown in FIG. 1, a unit casing 16 of the light-emitting unit 2 accommodates a light-emitting body 17 and a shade 18 therein. The light-emitting body 17 may utilize a flashlight that is composed of a xenon lamp, and the light has a function of adjusting growth of body hair (the function that controls growth of body hair in the present embodiment). The shade 18 is provided at a lower side of the light-emitting body 17, and reflects the light emitted from the light-emitting body 17 towards a light emitting direction "A" which denotes the upward direction in the figure. A light emitting opening 19 is formed in the portion that is located in the upper end of the unit casing 16 in the light emitting direction "A" of the light-emitting body 17. A transparent window 20 is installed in the light emitting opening 19 and the light from the light-emitting body 17 is emitted to outside through the window 20.

As shown in FIG. 2, the connector 21 is exposed from the lower end of the unit case 16. The connector 21, which is electrically connected to the light-emitting body 17, is connected electrically to the connector 11 of the device body 1 when the light-emitting unit 2 is locked to the device body 1. That is, in the state where the light-emitting unit 2 is locked to the device body 1, the light-emitting body 17 is electrically connected to the main capacitor part 9 within the body casing 7 through the connector 11 and the connector 21.

An operation for obtaining hair growth control effects by using the hair-growth adjusting light emitting device with the above configuration will be described below. Firstly, in the state where the light-emitting unit 2 is locked to the device body 1 as shown in FIG. 1, a user slides up the electric power switch 12 to turn on the electric power source. When the electric power switch 12 is powered on, the main capacitor part 9 accumulates electric charges. Secondly, the user makes the light emitting direction "A" of light-emitting unit 2 directed to a skin of the human body (not shown), a target for treatment, and then presses the upper end surface of the unit case 16 against the skin. When the user pushes the irradiation switch 13 to turn on the device, electric power is fed to the light-emitting body 17 from the main capacitor part 9 through the connector 11 and the connector 21, and then a pulse of light is emitted. Most of the light from the light-emitting body 17 travels toward the light emitting direction "A", and is emitted through the window 20 to outside. On the other hand, the remaining light, not traveling toward the light emitted direction "A", is reflected by the shade 11 and is emitted through the window 20 to outside.

Figure 7A:
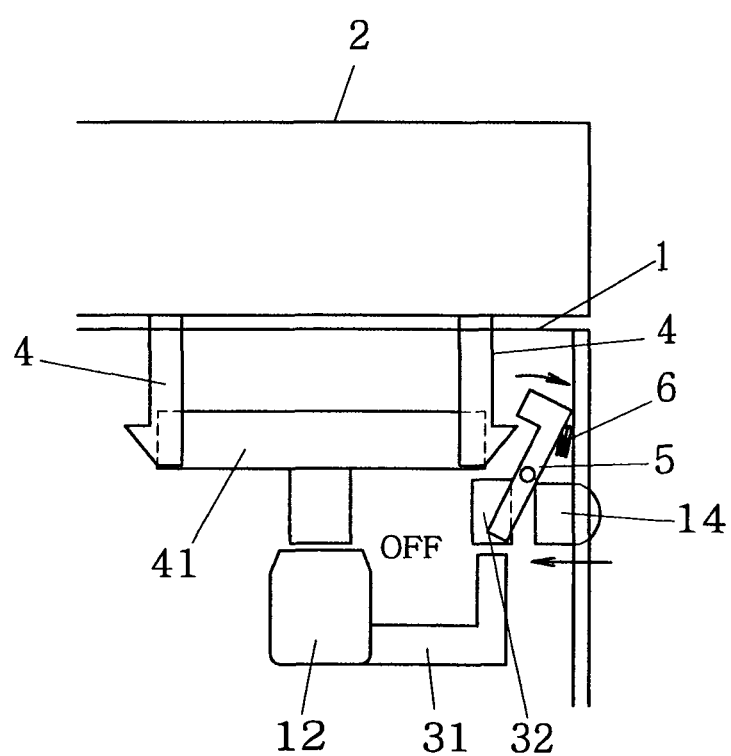
Figure 7B:
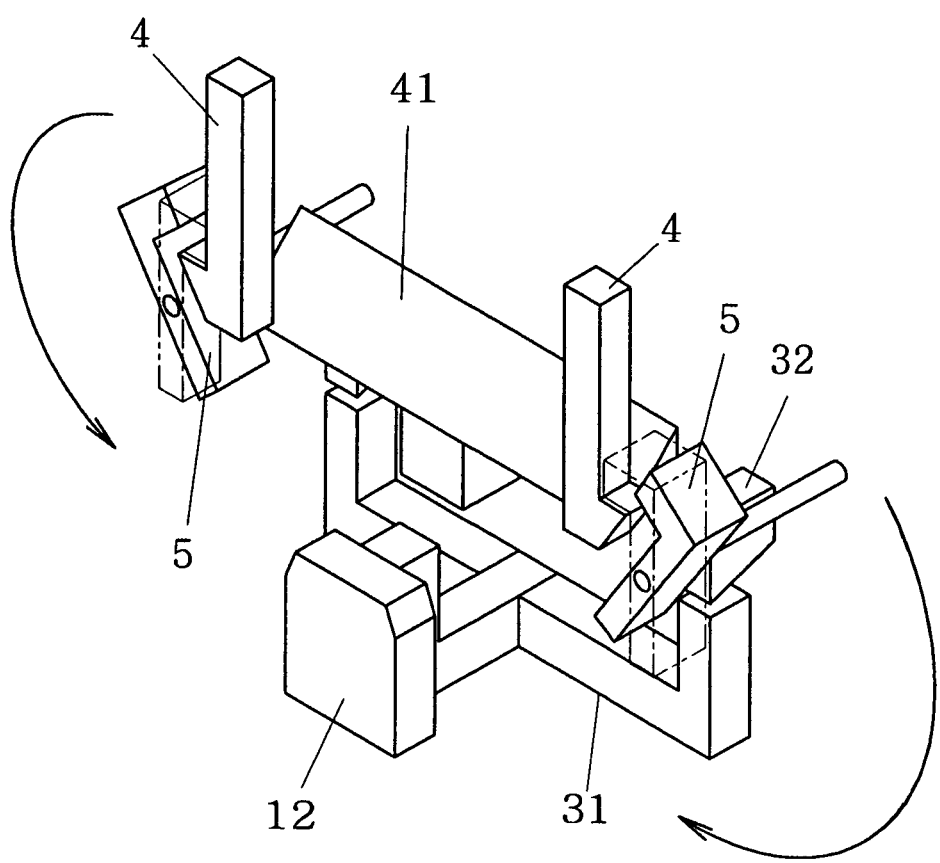
Figure 8A:
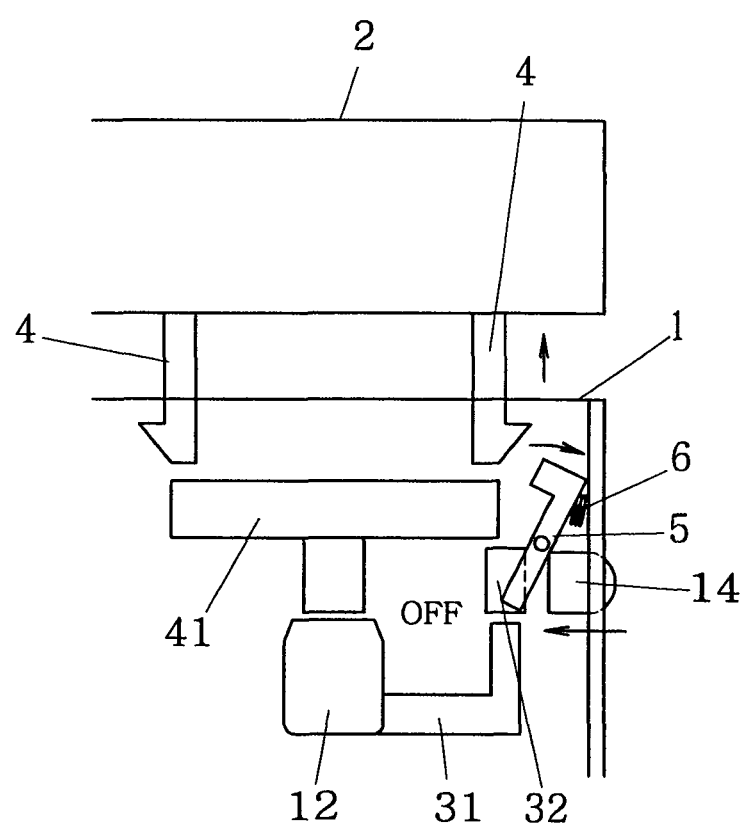
FIG. 8A is an explanatory view (top view) of a main section showing the state of detaching the light-emitting unit of the hair-growth adjusting light emitting device.
Figure 8B:
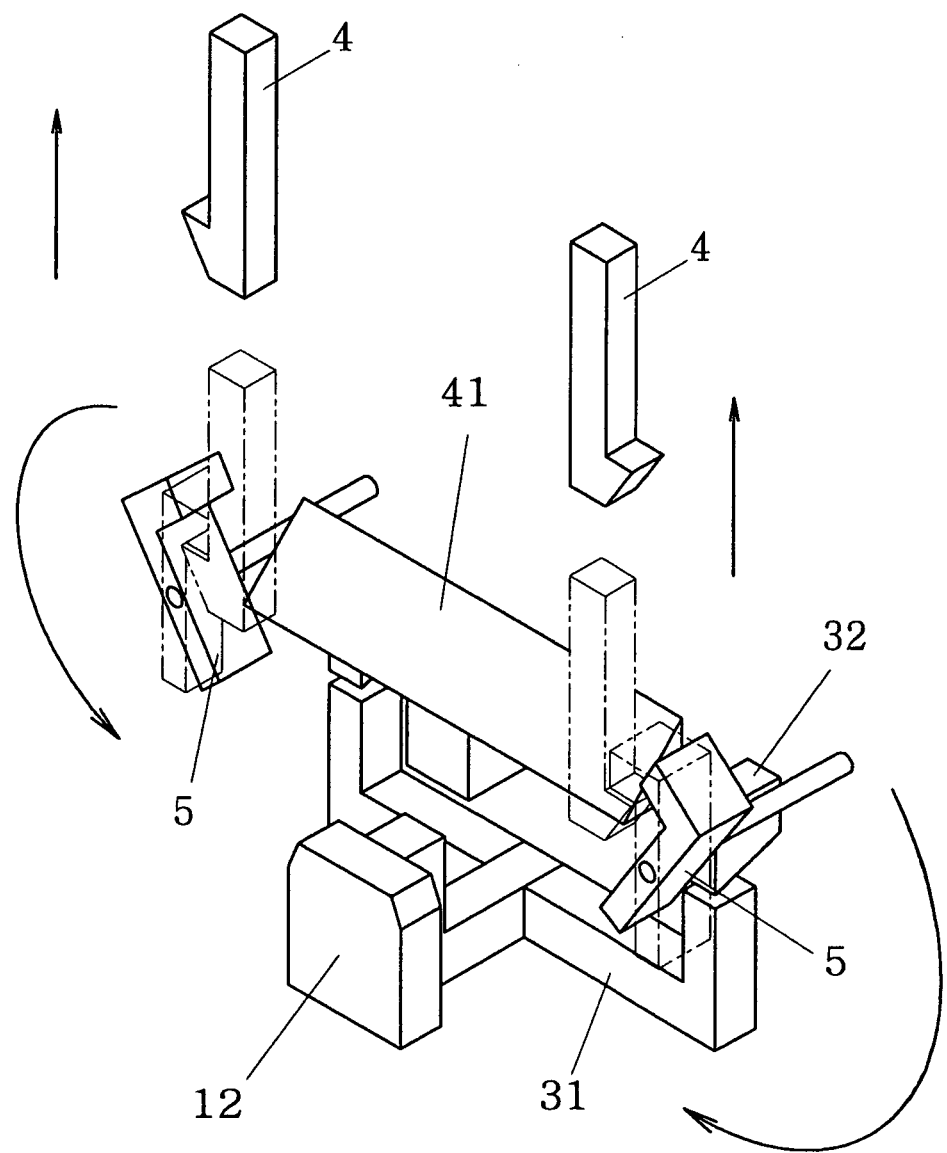
FIG. 8B is an explanatory view (perspective view) of a main section showing the state of detaching the light-emitting unit of the hair-growth adjusting light emitting device.

The procedure of replacing the light-emitting unit 2 of the hair-growth adjusting light emitting device with the above-mentioned configuration will be described below. At first, the user pushes inwardly the release buttons 14, which are located in both of right and left sides of the body casing 7, in the right and left direction. When the release button 14 is pushed into the body casing 7 as shown in FIGS. 7A and 7B, a lower portion of the locking part 5 is pressed by the bottom of the release button 14. The locking part 5 moves pivotally about the pivotal shaft against the biasing force of the biasing member 6, and the upper end portion thereof is moved toward the side wall of the body casing 7. With such movement, as shown in FIG. 8A and FIG. 8B, the engagement between the locked part 4 and the locking part 5 is released, and the light-emitting unit 2 can be detached from the device body 1.

Furthermore, the hair-growth adjusting light emitting device of the present embodiment includes a release restriction mechanism 30 that controls an operation of releasing the lock of the light-emitting unit 2 by the release button 14, and a power-on restriction mechanism 40 that controls an operation of turning on the electric power source by the electric power switch 12.

The release restriction mechanism 30 is a mechanical control means capable of releasing the lock of the light-emitting unit 2 by the release button 14, only when the electric power switch 12 is in a power-off position. In other words, the release restriction mechanism 30 prevents the lock of the light-emitting unit 2 from being released by the release button 14 when the electric power switch 12 is in the power-on position. As specifically shown in FIG. 4, the release restriction mechanism 30, includes a pair of arms 31 with an L shape, a pair of release restriction members 32, and a pair of biasing members 33. The arms 31, 31 with an L shape extend from the electric power switch 12 to both of the right and left sides of the body casing 7. The release restriction member 32 is disposed within the body casing 7 so as to move freely in the forward and backward direction. When the electric power switch 12 is in the power-on position, the release restriction member 32 is pushed up to the front side of the body casing 7 by the arm 31, and then reaches a release prohibiting position. Herein, the release prohibiting position is located in an upper side (the front side of the body casing 7) relative to the release restriction member 32 within the body casing 7. The biasing member 33 is configured by a compression spring biasing the release restriction member 32 from the release prohibiting position to the backside of the body casing 7. That is, in the power-off state, the release restriction member 32 is pressed toward the backside of the body casing 7 by the biasing member 33. In the power-on state, the release restriction member 32 is pushed up to the front side of the body casing 7 by the arm 31 against the biasing force of the biasing member 33.

Note that the release prohibiting position of release restriction member 32 in the present embodiment denotes a position satisfying the following two states (first and second states) at the same time. Namely, in the first state, the release restriction member 32, the lower portion of the locking part 5, and the release button 14 are lined up in this order along the right and left direction of the body casing 7, as shown in FIG. 2. In the second state, these three members are arranged within the surface perpendicular to the forward and backward direction of the body casing 7, as shown in FIG. 5. When the release restriction member 32 is in the release prohibiting position, the locking part 5 cannot move pivotally due to the release restriction member 32 contacting therewith, even when the release button 14 pushes the lower end part thereof. Accordingly, the locking part 5 cannot be released from the engagement with the locked member 4 and the light-emitting unit 2 cannot be detached from the device body 1.

Figure 4:
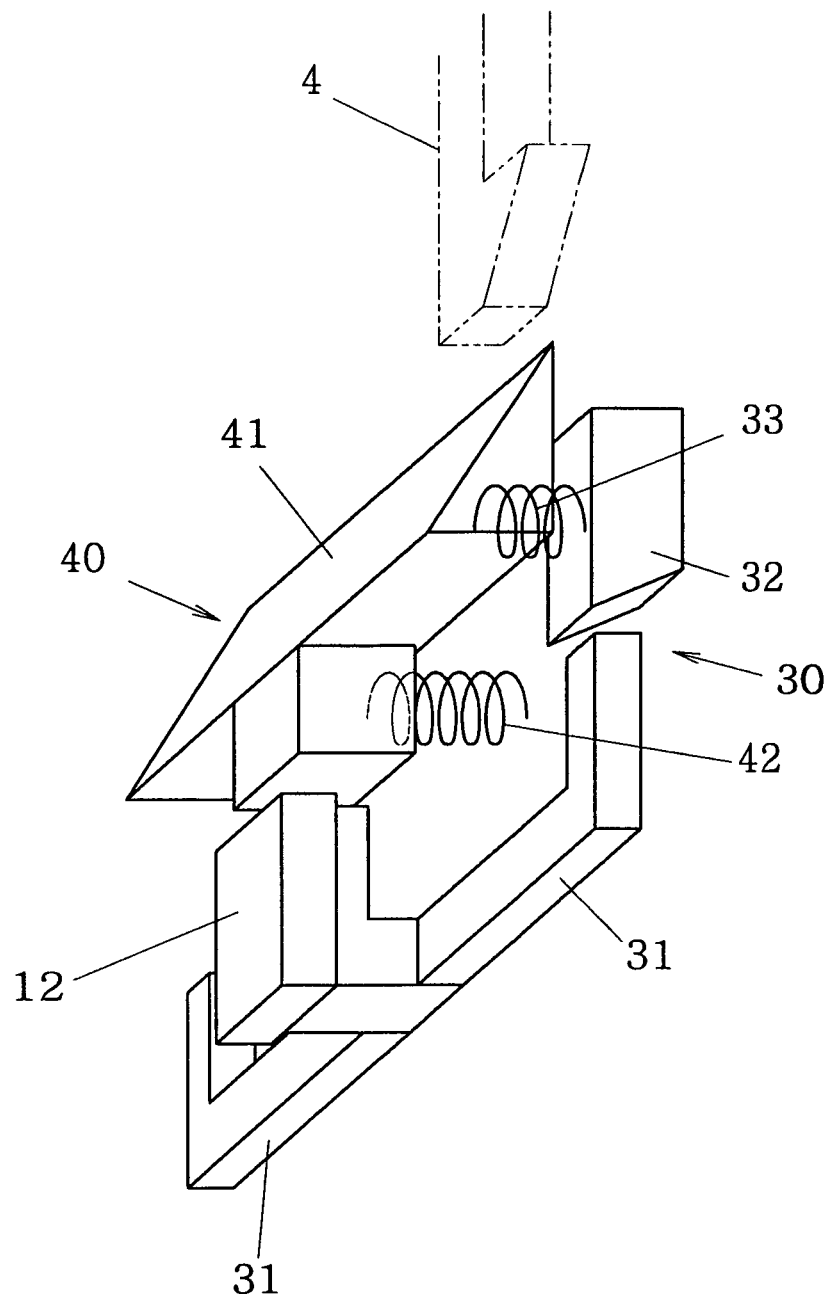
FIG. 4 is an explanatory view showing main sections of the release restriction mechanism and the power-on restriction mechanism of the hair-growth adjusting light emitting device.

The power-on restriction mechanism 40 is a mechanical control means for enabling the electric power switch 12 to turn on the electric power source only when the light-emitting unit 2 is locked to the device body 1, while preventing the electric power switch 12 from being turned on when the light-emitting unit 2 is detached from the device body 1. As specifically shown in FIG. 4, the power-on restriction mechanism 40 includes a power-on restriction member 41 and a biasing member 42. FIG. 4 shows the state where the electric power switch 12 is in the power-off position. The power-on restriction member 41 is provided movably along the forward and backward direction of the body casing 7. When the light-emitting unit 2 is locked to the device body 1, the power-on restriction member 41 is pushed backwardly in the forward and backward direction by the tip of the locked member 4 contacting with the power-on restriction member 41. When the power-on restriction member 41 is in a power-on prohibiting position, the electric power switch 12 contacts with the power-on restriction member 41, so that it cannot be moved. With this configuration, the user cannot slide the electric power switch 12, thereby disabling to turn on, even if trying to slide the electric power switch 12 from the lower position (power-off position) to the upper position (power-on position) for powering on. Note that the power-on prohibiting position denotes a forward position relative to the power-on restriction member 41 in the forward and backward direction of the body casing 7, and a power-on possible position denotes a backward position in the forward and backward direction of the body casing 7. The biasing member 42 is also configured by a compression spring that energizes for pushing the power-on restriction member 41 to the power-on prohibiting position, when the light-emitting unit 2 is detached from device body 1.

Hereinafter, with reference to FIGS. 5 to 8, there will be described the operation of detaching the light-emitting unit 2 from the device body 1.

Figure 5A:
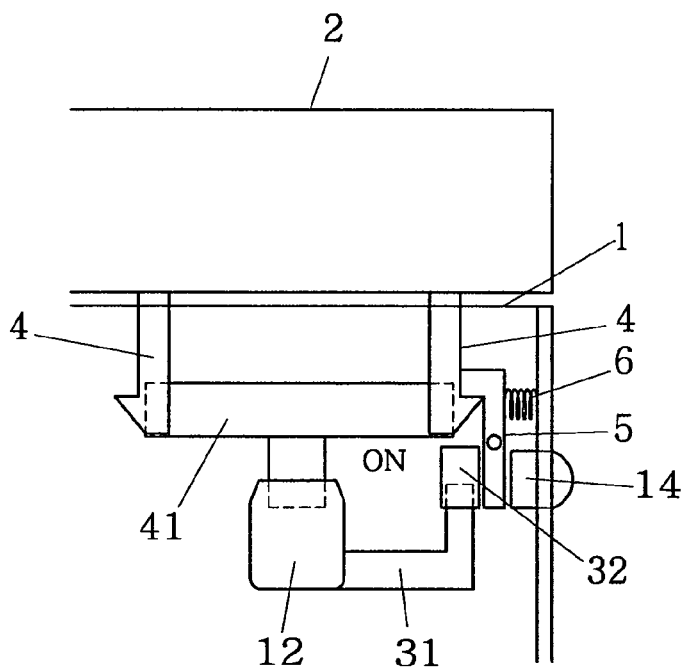
Figure 5B:
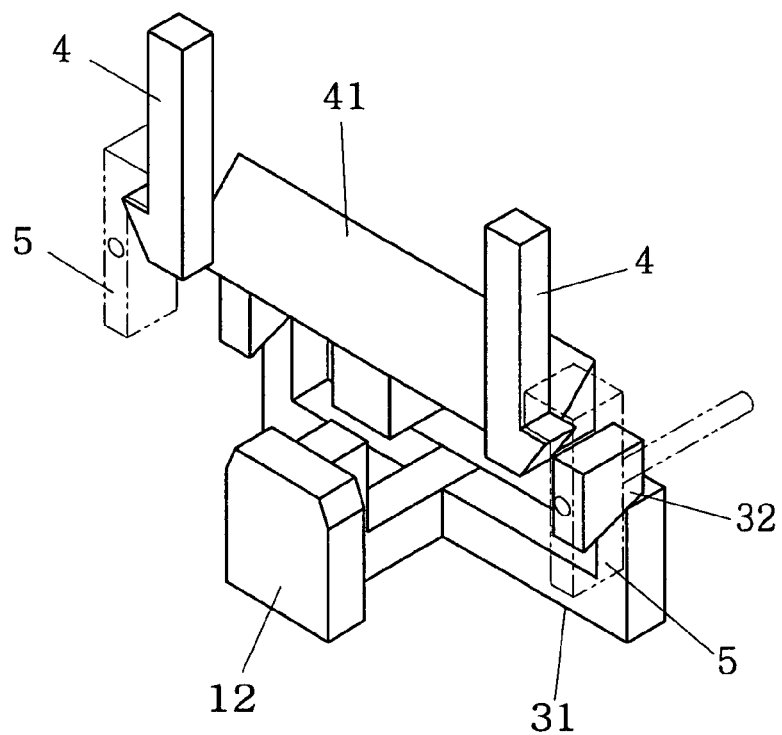
Figure 5C:
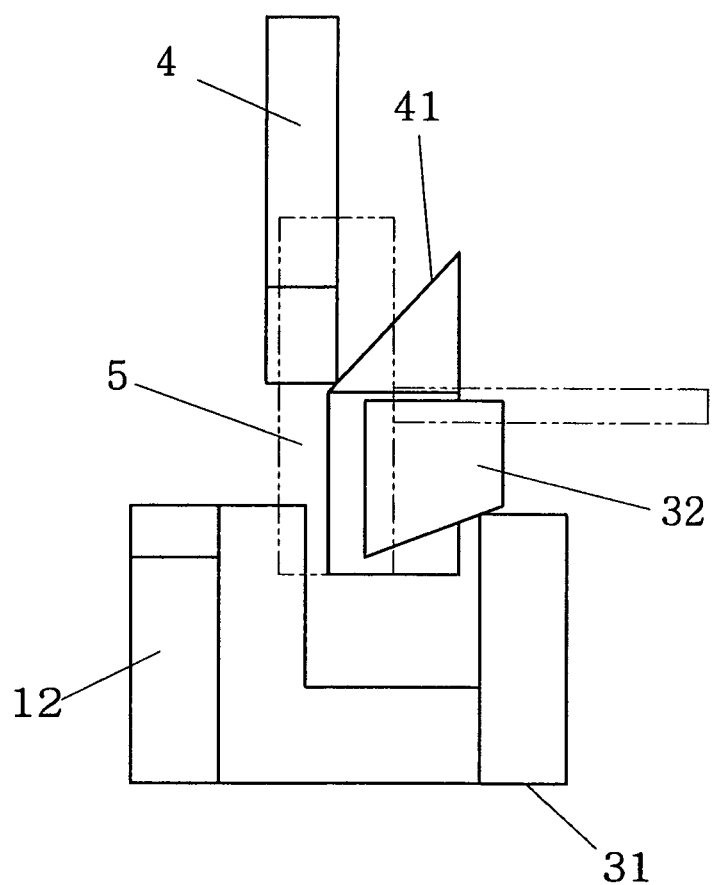

FIGS. 5A to 5C show the state where the light-emitting unit 2 is attached to the device body 1. Firstly, in FIG. 5, the locked member 4 is in contact with the power-on restriction member 41 to depress the power-on restriction member 41 toward the backside of the body casing 7. As shown in FIGS. 5B and 5C, when being located in the backside of the body casing 7, the power-on restriction member 41 has no contact with the electric power switch 12. Accordingly, the electric power switch 12 can slide to both the power-on position and the power-off position. FIGS. 5A to 5C show the state where the electric power switch 12 is in the power-on position. Referring to FIGS. 5B and 5C, the release restriction member 32 is pushed up to the front side position of the body casing 7 by the arm 31, i.e., the release prohibiting position. The lower end part of the locking part 5 and the release restriction member 32 are brought into contact when the release restriction member 32 is in the release prohibiting position. Therefore, the locking part 5 cannot move pivotally even when being pushed by the release button 14. Accordingly, in the state of FIGS. 5A to 5C, even if the user pushes the release button 14, the light-emitting unit 2 cannot be detached from the device body 1.

Figure 6A:
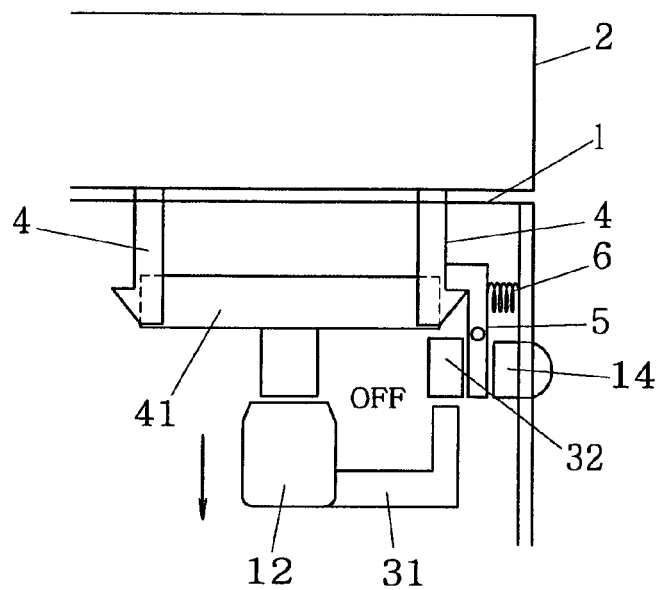
FIG. 6A is an explanatory view (top view) showing a main section of the hair-growth adjusting light emitting device when being turned off.
Figure 6B:
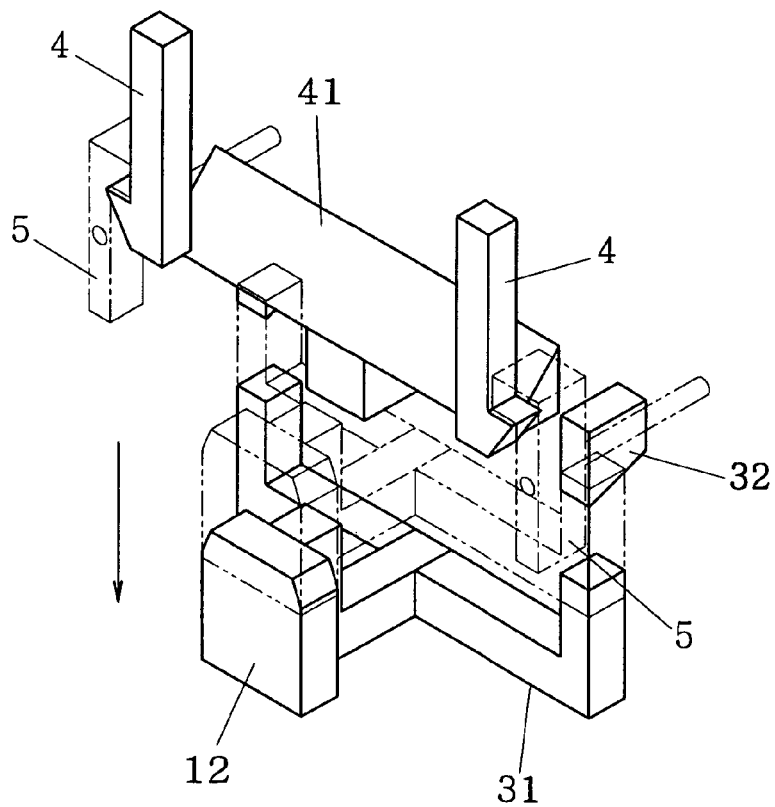
FIG. 6B is an explanatory view (perspective view) showing a main section of the hair-growth adjusting light emitting device when being turned off.
Figure 6C:
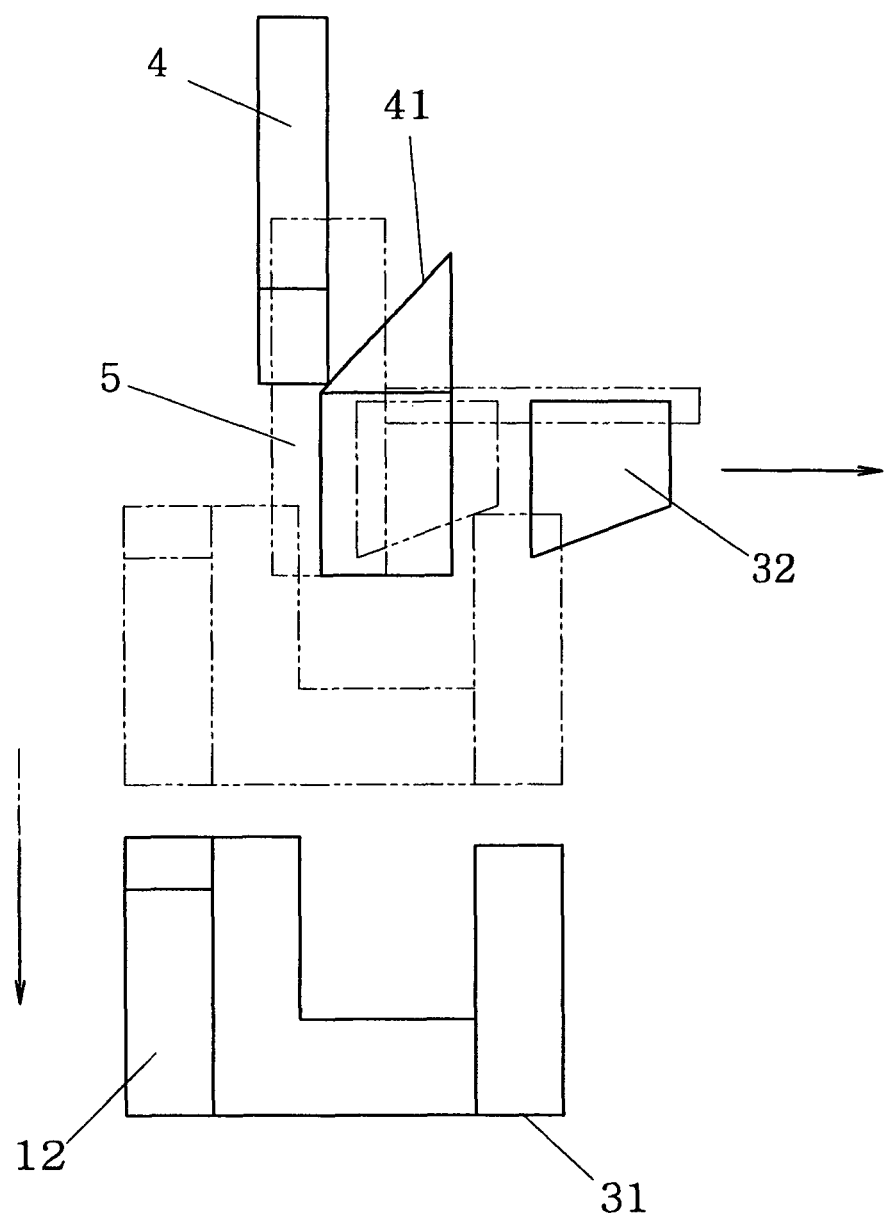
FIG. 6C is an explanatory view (side view) showing a main section of the hair-growth adjusting light emitting device when being turned off.

Secondly, the electric power switch 12 is slid down to the power-off position and then powered off. At the time, as shown in FIGS. 6A to 6C, since the arm 31 is separated from the release restriction member 32, the biasing force of the biasing member 33 pushes the release restriction member 32 from the release prohibiting position to the backside of the body casing 7. That is, the locking part 5 has no contact with the release restriction member 32, enabling to move pivotally, in the state where the release restriction member 32 is pushed to the backside of the body casing 7.

Figure 7C:
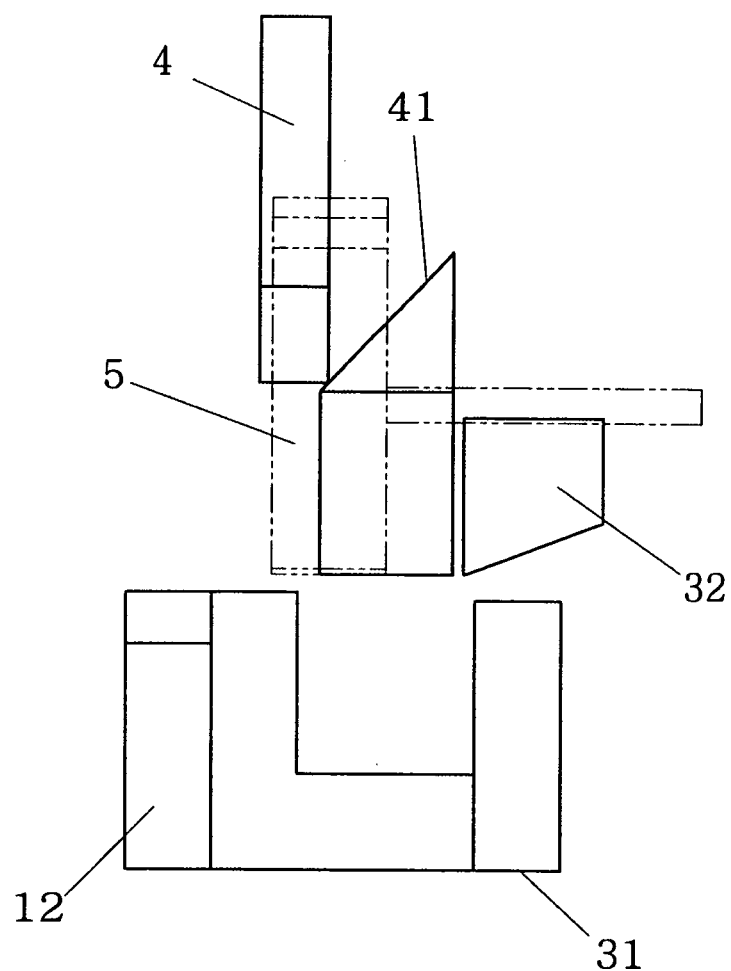
Figure 8C:
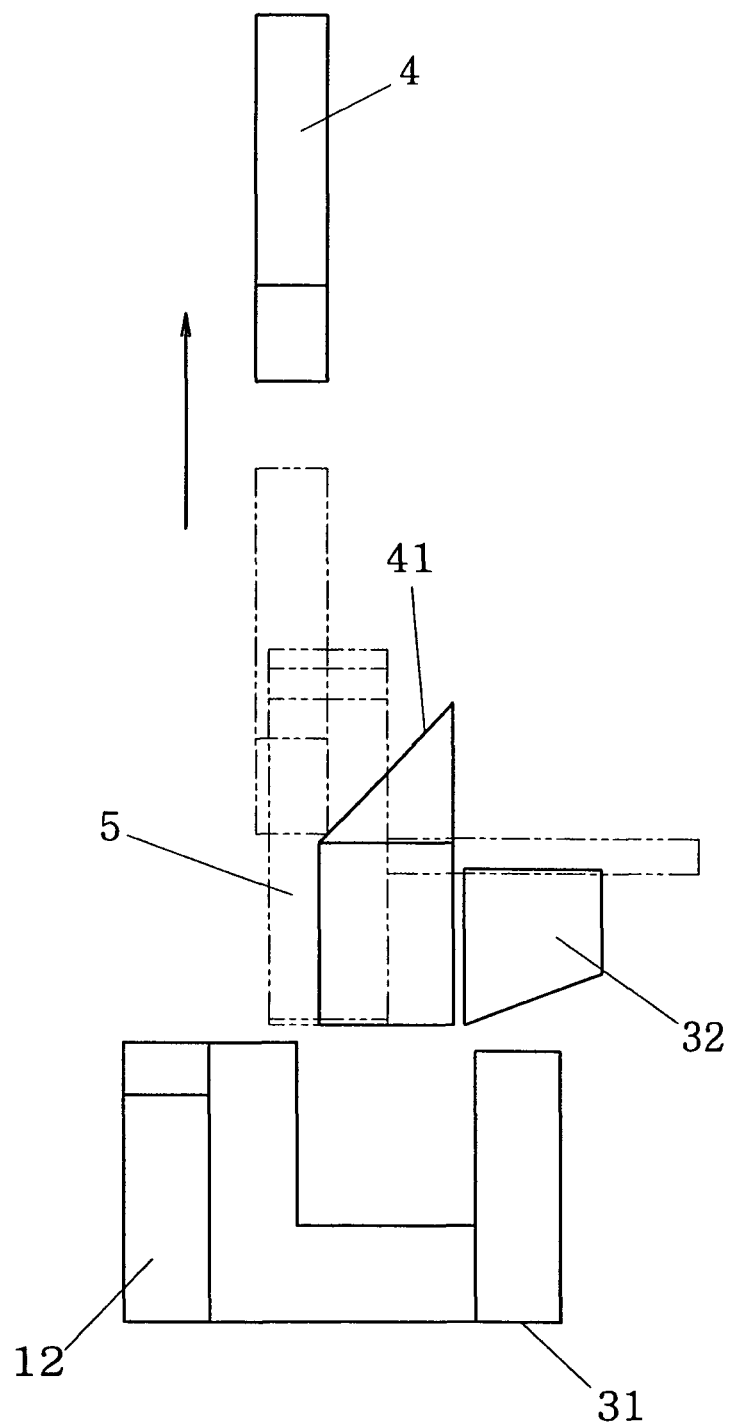
FIG. 8C is an explanatory view (side view) of a main section showing the state of detaching the light-emitting unit of the hair-growth adjusting light emitting device.

In this situation, as shown in FIGS. 7A to 7C, when the release button 14 is pushed in, the locking part 5 is released from the engagement with the locked member 4 because it is moved pivotally against the biasing force of the biasing member 6. As shown in FIGS. 8A to 8C, when the light-emitting unit 2 is drawn out upwardly while the release button 14 is pushed in, the light-emitting unit 2 can be detached from the device body 1.

As above mentioned, in the state where the electric power switch 12 remains turned on, the release button 14 cannot be pushed in due to the release restriction member 32 located at the release prohibiting position. That is, the light-emitting unit 2 is surely prevented from being detached from the device body 1 in the state where the electric power source remains turned on.

Figure 9:
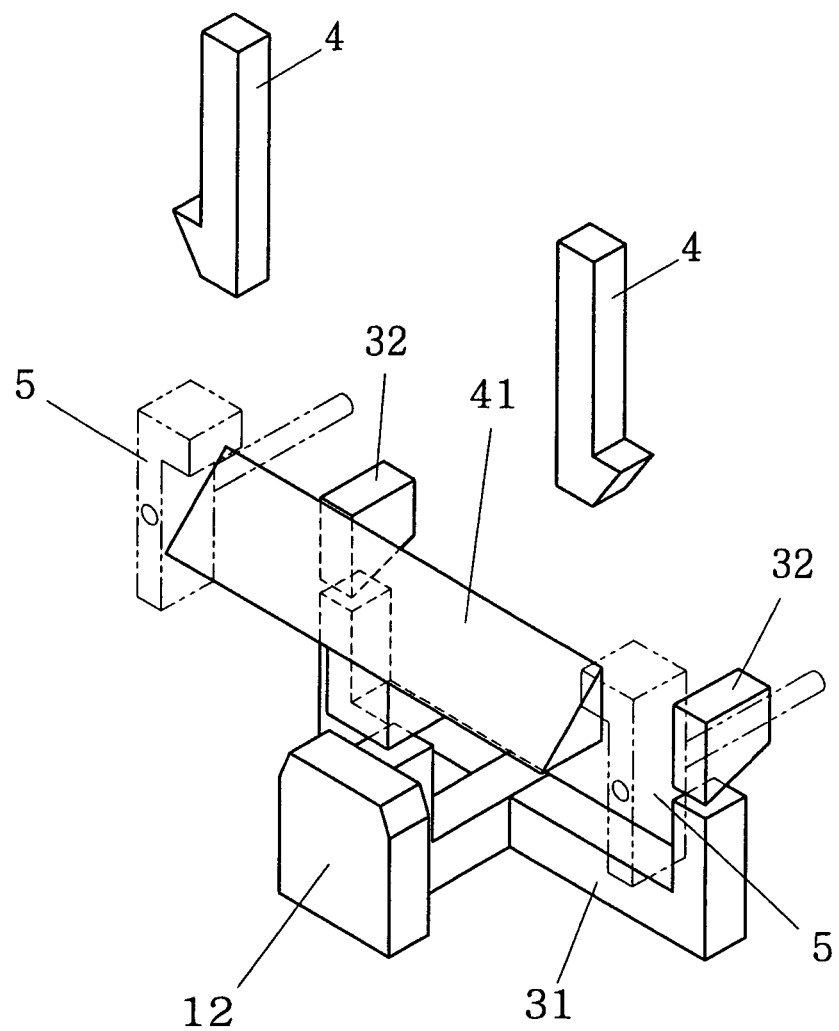
FIG. 9 is an explanatory view (perspective view) of a main section showing the state where the light-emitting unit of the hair-growth adjusting light emitting device is removed.

In the state where the light-emitting unit 2 is removed from device body 1 as shown in FIG. 9, the biasing force of the biasing member 42 forces the power-on restriction member 41 to the power-on prohibiting position. When the power-on restriction member 41 is in the power-on prohibiting position, the electric power switch 12 is brought into contact with the power-on restriction member 41, so that it cannot be moved to the power-on position. That is, it is surely prevented to turn on the electric power source in the state where the connector 11 is exposed.

Furthermore, the hair-growth adjusting light emitting device of the present embodiment further includes a discharge control part 50 that discharges the electric charges in the main capacitor part 9 by using the discharging circuit part 15, when the electric power switch 12 is turned off. The discharge control part 50 has a control part 25. The discharge control part 50 is configured to turn off the electric power source based on operation signals from the electric power switch 12 and, at the same time, discharge the electric charges in the main capacitor part 9 by using the discharging circuit part 15.

The hair-growth adjusting light emitting device with the above-mentioned configuration includes the release restriction mechanism 30, the power-on restriction mechanism 40, and the discharge control part 50. The control part 25 discharges the electric charges in the main capacitor part 9 every time when the electric power switch 12 is turned off. Accordingly, even if a user without expert knowledge of electric appliances replaces the light-emitting unit, it is possible to prevent a dangerous occurrence, like sparking in an electric contact, with reliability.

The control part 25 may discharge the electric charges in the main capacitor part 9 in synchronization with a push-in movement of the release button 14. In this case, a release detecting sensor (not shown) that detects the push-in movement of the release button 14 may be provided in the device body 1, and the control part 25 may allow the discharging circuit part 15 to discharge the electric charges in the main capacitor part 9 based on the detection signal of the release detecting sensor.

Furthermore, the light-emitting body 17 is not limited to a flashlight made of a xenon light, and may utilize a flashlight with any other configurations, or may emit a laser beam utilizing a laser diode etc. Besides, the light-emitting body 17 may emit light for obtaining hair-growing effects by promoting hair growth of body hair.

While the invention has been shown and described with respect to the preferred embodiments, it will be understood by those skilled in the art that various changes and modification may be made without departing from the scope of the invention as defined in the following claims.

The invention claimed is:

1. A light emitting device, comprising:
   a device body,
   a light-emitting unit removably attached to the device body, and
   a locking unit for locking the light-emitting unit to the device body;
   wherein the device body comprises:
   an electric power supplying part,
   a first connector electrically connected to the electric power supplying part,
   an electric power switch that switches on and off an electric power supplied from the electric power supplying part to the first connector, and
   a release member for releasing the lock of the light-emitting unit by the locking unit;
   the light-emitting unit comprises:
   a light emitting body emitting a light, and
   a second connector electrically connected to the first connector when the light-emitting unit is locked to the device body, and feeding electric power from the first connector to the light emitting body; and
   the light emitting device further comprises:
   a release restriction mechanism including a release restriction member, which is positioned at a release prohibiting position by the electric power switch in a state where the electric power switch is at a power-on position where the electric power supplying part feeds the electric power to the first connector, wherein the release restriction member positioned at the release prohibiting position restricts movement of the release member such that the lock of the light emitting unit is not allowed to be released by the release member, and
   a power-on restriction mechanism including a power-on restriction member, which is positioned at a power-on prohibiting position in a state where the light-emitting unit is detached from the device body, wherein the power-on restriction member positioned at the power-on prohibiting position restricts movement of the electric power switch such that the electric power switch is not allowed to be moved from a power-off position to the power-on position, and
   wherein the power-on restriction member is moved by the locking unit.

2. The light emitting device as set forth in claim 1, wherein the electric power supplying part comprises:
   a booster circuit part for boosting electric power from an electric power source;
   a capacitor part for accumulating the boosted electric power and supplying the accumulated electric power to the first connector;
   a discharge circuit part for discharging the electric power accumulated in the capacitor part; and
   a discharge control part for controlling the discharge circuit part to discharge the electric power in the capacitor part in the state where the electric power switch is at a power-off position where the electric power supplying part stops feeding the electric power to the first connector.

3. The light emitting device as set forth in claim 1, wherein the electric power switch makes translation motion.

4. The light emitting device as set forth in claim 3, wherein the release restriction mechanism further includes an arm of L shape extending from the electric power switch, the arm pushing the release restriction member to the release prohibiting position when the electric power switch moves from the power-off position to the power-on position.

5. The light emitting device as set forth in claim 4, wherein the release restriction mechanism further includes a biasing member forcing the release restriction member to be positioned out of the release prohibiting position when the electric power switch is at the power-off position.

6. The light emitting device as set forth in claim 1, wherein the locking unit includes a locked part and a locking part, the locked part and the locking part being engaged with each other by hooks thereof, and
   wherein the locking part is pivotally moved when the release member is pushed.

7. The light emitting device as set forth in claim 6, wherein the locking part is not allowed to be moved pivotally when the release restriction member is positioned at the release prohibiting position.

8. The light emitting device as set forth in claim 1, wherein the power-on restriction mechanism further includes a biasing member forcing the power-on restriction member to be positioned at the power-on prohibiting position in a state where the light-emitting unit is detached from the device body.

9. The light emitting device as set forth in claim 8, wherein the locking unit forces the power-on restriction member to be out of the power-on prohibiting position in a state where the light-emitting unit is attached to the device body.

10. The light emitting device as set forth in claim 1, wherein the light emitting device is a hair-growing adjusting device for use in irradiating a human skin with the light to adjust growth of body hair.

* * * * *